(12) United States Patent
Shelton et al.

(10) Patent No.: US 8,603,050 B2
(45) Date of Patent: Dec. 10, 2013

(54) IMPLANTABLE INFUSION DEVICES INCLUDING APPARATUS FOR CONFIRMING SIDE PORT ACCESS

(75) Inventors: Brian Michael Shelton, Northridge, CA (US); Scott R. Gibson, Granada Hills, CA (US); Lawrence S. Ring, Valencia, CA (US); Paul Edward Ross, Glendale, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 836 days.

(21) Appl. No.: 11/759,882

(22) Filed: Jun. 7, 2007

(65) Prior Publication Data
US 2008/0306466 A1 Dec. 11, 2008

(51) Int. Cl.
*A61M 37/00* (2006.01)
(52) U.S. Cl.
USPC .................................... 604/288.01

(58) Field of Classification Search
USPC .................... 604/502, 288.02, 505, 508, 507, 604/288.03, 288.01
See application file for complete search history.

(56) References Cited

U.S. PATENT DOCUMENTS

| 5,006,997 | A | 4/1991 | Reich | |
|---|---|---|---|---|
| 6,962,580 | B2 * | 11/2005 | Adams et al. | 604/891.1 |
| 7,070,591 | B2 | 7/2006 | Adams et al. | |
| 2005/0075624 | A1 | 4/2005 | Miesel | |
| 2006/0089619 | A1 * | 4/2006 | Ginggen | 604/891.1 |
| 2008/0243093 | A1 * | 10/2008 | Kalpin et al. | 604/288.02 |

* cited by examiner

*Primary Examiner* — Kevin C Sirmons
*Assistant Examiner* — Brandy S Lee
(74) *Attorney, Agent, or Firm* — Henricks, Slavin & Holmes LLP

(57) ABSTRACT

Implantable infusion devices and systems with side port access detection capability and methods of detecting side port access. The methods may include the steps of sensing pressure in a fluid passage between an implanted pump mechanism and an implanted outlet port and determining that an implanted side port has been accessed by a hypodermic needle based on a predetermined change in pressure in the fluid passage between the implanted pump mechanism and the implanted outlet port.

22 Claims, 3 Drawing Sheets

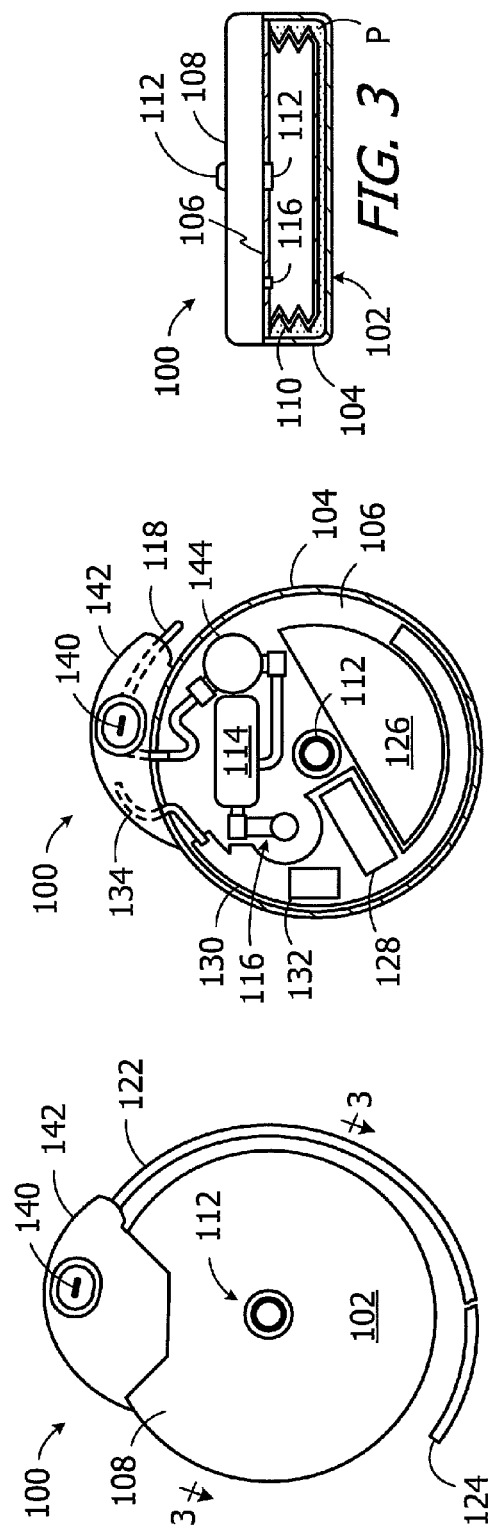

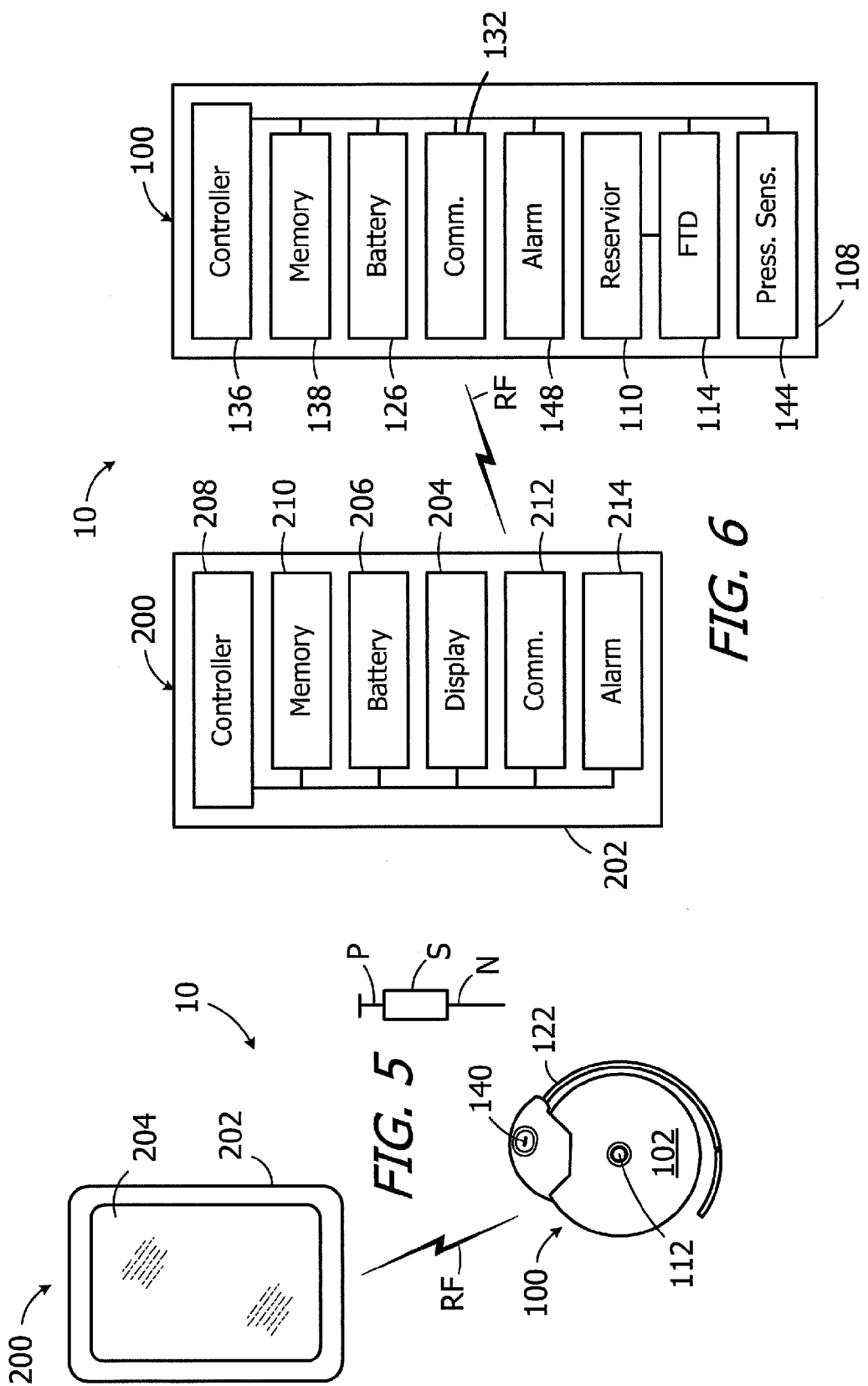

US 8,603,050 B2

IMPLANTABLE INFUSION DEVICES INCLUDING APPARATUS FOR CONFIRMING SIDE PORT ACCESS

BACKGROUND OF THE INVENTIONS

1. Field of Inventions

The present inventions relate generally to implantable infusion devices.

2. Description of the Related Art

Implantable infusion devices have been used to provide patients with a medication or other substance (collectively "infusible substance") and frequently include a reservoir and a pump. The reservoir is used to store the infusible substance and, in some instances, implantable infusion devices are provided with a refill port that allows the reservoir to be transcutaneously filled (and/or re-filled) with a hypodermic needle. The reservoir is coupled to the pump, which is in turn connected to an outlet port. A catheter, which has an outlet at the target body region, may be connected to the outlet port. As such, infusible substance from the reservoir may be transferred from the reservoir to the target body region by way of the pump and catheter.

Implantable infusion devices may also include a side port that facilitates access to the outlet port and catheter. The side port, which is typically accessed by way of a hypodermic needle, allows the clinician to push fluid into the catheter or draw fluid from the catheter to check for catheter occlusion, sample cerebrospinal fluid (CSF), inject contrast dye into the patient and/or catheter for use during a fluoroscopic procedure, remove medication from the catheter prior to dye injection, inject additional medication into the target region at the catheter outlet and/or remove pharmaceuticals or other fluids that are causing an allergic or otherwise undesirable biologic reaction. The side port is frequently located at the outer perimeter of the infusion device in order to increase the likelihood that the side port will be tactilely distinguished from the refill port.

Accessing the side port with a hypodermic needle can, however, be difficult. For example, the outer perimeter location of the side port can make access difficult and, in those instances where the patient is obese, it can be difficult to tactilely distinguish the side port from the refill port. As a result, clinicians may incorrectly determine that the refill port has been accessed, when in fact the side port has been accessed, and vice versa. Such incorrect access determinations can lead to refill medication being delivered to the side port instead of the refill port and/or contrast dye being delivered to the refill port instead of the side port. Incorrect access determinations can also lead to medication and contrast dye being delivered to the wrong location within the patient's body when no port is accessed, e.g. to pump pocket instead of to the region near the catheter outlet. Incorrect side port access determinations can also result in an unfounded catheter patency verification. In the exemplary context of medication delivery to the intrathecal space, the clinician may draw a clear fluid (e.g. serous fluid from the abdomen) into a syringe when side port has not been properly accessed. The clear fluid may be mistaken for CSF from the intrathecal space which, in turn, may lead the clinician to determine that a catheter is not blocked without actually having drawn fluid from the catheter.

Accordingly, the present inventors have determined it would be desirable to provide the clinician with confirmation that the side port has been successfully accessed.

SUMMARY OF THE INVENTIONS

The present apparatus and methods employ pressure measurements to confirm that a side port has been accessed. In one implementation, the present apparatus and methods use a pressure sensor associated with the outlet port, which may also be used to detect catheter blockages, to detect side port access. As such, the present apparatus and methods confirm side port access without requiring the use of additional sensors or other structural elements that would be used solely for the purpose of confirming side port access.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a plan view of the implantable infusion device illustrated in FIG. 1 with the cover removed.

FIG. 3 is a partial section view taken along line 3-3 in FIG. 1.

FIG. 4 is a block diagram of the implantable infusion device illustrated in FIGS. 1-3.

FIG. 5 is a plan view of an implantable infusion device system in accordance with one embodiment of a present invention.

FIG. 6 is a block diagram of the implantable infusion device system illustrated in FIG. 5.

DETAILED DESCRIPTION OF THE EXEMPLARY EMBODIMENTS

Figure 7:
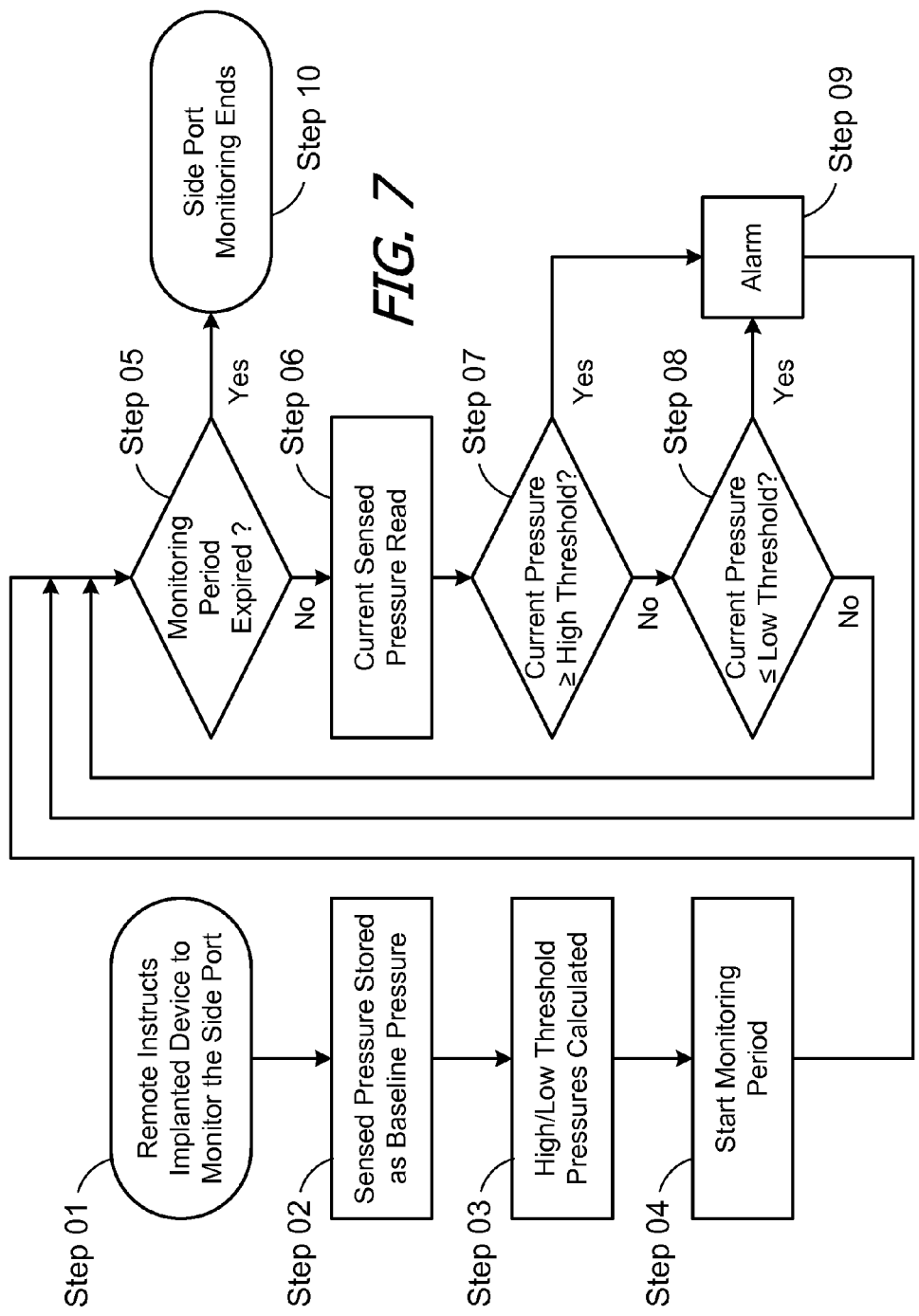
FIG. 7 is a flow chart illustrating a method in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion device described herein and, instead, are applicable to other implantable infusion devices that currently exist or are yet to be developed.

One example of an implantable infusion device in accordance with a present invention is generally represented by reference numeral 100 in FIGS. 1-4. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a refill port 112 that extends from the reservoir, through the internal wall 106, to the cover 108. A hypodermic needle (not shown), which is configured to be pushed through the refill port 112, may be used to replenish the reservoir 110.

A wide variety of reservoirs may be employed. In the illustrated embodiment, the reservoir 110 is in the form of a titanium bellows that is positioned within a sealed volume defined by the housing bottom portion 104 and internal wall 106. The remainder of the sealed volume is occupied by propellant P, which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 100 illustrated in FIGS. 1-4 also includes a fluid transfer device 114. The inlet of a fluid transfer device 114 is coupled to the interior of the reservoir 110 by a passageway 116, while the outlet of the fluid transfer device is coupled to an outlet port 118 by a passageway 120. Operation of the fluid transfer device 114 causes infusible substance to move from the reservoir 110 to the outlet port 118. A catheter 122 may be connected to the outlet port 118 so that the infusible substance passing through the outlet port will be delivered to a target body region in spaced relation to the infusion device 100 by way of the outlet 124 at the end of the catheter.

A wide variety of fluid transfer devices may be employed. In the illustrated embodiment, the fluid transfer device 114 is in the form of an electromagnet pump. The present inventions are not, however, limited to electromagnet pumps and may include other types of fluid transfer devices. Such devices include, but are not limited to, other electromagnetic pumps, solenoid pumps, piezo pumps, and any other mechanical or electromechanical pulsatile pump. In the exemplary context of implantable drug delivery devices, and although the volume/stroke magnitude may be increased in certain situations, the fluid transfer devices will typically deliver about 1 microliter/stroke, but may be more or less depending on the particular fluid transfer device employed. Additionally, although the exemplary fluid transfer device 114 is provided with internal valves (e.g. a main check valve and a bypass valve), valves may also be provided as separate structural elements that are positioned upstream of and/or downstream from the associated fluid transfer device.

Energy for the fluid transfer device 114, as well for other aspects of the exemplary infusion device 100, is provided by the battery 126 illustrated in FIG. 2. In the specific case of the fluid transfer device 114, the battery 126 is used to charge one or more capacitors 128, and is not directly connected to the fluid transfer device itself. The capacitor(s) 128 are connected to an electromagnet coil in the fluid transfer device 114, and disconnected from the battery 126, when the electromagnet coil is being energized, and are disconnected from the electromagnet coil and connected to the battery when the capacitor(s) are being recharged and/or when the fluid transfer device is at rest. The capacitor(s) 128 are carried on a board 130. A communication device 132, which is connected to an antenna 134, is carried on the same side of the board 130 as the capacitor(s) 128. The exemplary communication device 132 is an RF communication device. Other suitable communication devices include, but are not limited to, oscillating magnetic field communication devices, static magnetic field communication devices, optical communication devices, ultrasound communication devices and direct electrical communication devices.

A controller 136 (FIG. 4), such as a microprocessor, microcontroller or other control circuitry, is carried on the other side of the board 130. The controller controls the operations of the infusion device 100 in accordance with instructions stored in memory 138 and/or provided by an external device (e.g. the remote control 200 described below) by way of the communication device 132. For example, the controller 136 may be used to control the fluid transfer device 114 to supply fluid to the patient in accordance with, for example, a stored basal delivery schedule or a bolus delivery request. The controller 136 may also be used to monitor sensed pressure in the manner described below.

Referring to FIGS. 1, 2 and 4, the exemplary infusion device 100 is also provided with a side port 140 that is connected to the passageway 120 between the outlet of the fluid transfer device 114 and the outlet port 118. The side port 140 facilitates access to an implanted catheter 122, typically by way of a hypodermic needle. For example, the side port 140 allows clinicians to push fluid into the catheter 122 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 124, and/or removing pharmaceuticals or other fluids that are causing an allergic or otherwise undesirable biologic reaction.

The outlet port 118, a portion of the passageway 120, the antenna 134 and the side port 140 are carried by a header assembly 142. The header assembly 142 is a molded, plastic structure that is secured to the housing 102. The housing 102 includes a small aperture through which portions of the passageway 120 are connected to one another, and a small aperture through which the antenna 134 is connected to the board 130.

The exemplary infusion device 100 illustrated in FIGS. 1-4 also includes a pressure sensor 144 that is connected to the passageway 120 between the outlet of the fluid transfer device 114 and the outlet port 118. As such, the pressure sensor 144 senses the pressure at the outlet port 118 which, in the illustrated embodiment, is also the pressure within the catheter 122. The pressure sensor 144 is connected to the controller 136 and may be used to analyze a variety of aspects of the operation of the exemplary implantable infusion device 100. For example, pressure measurements may be used to determine whether or not the fluid transfer device 114 is functioning properly and whether or not there is a complete or partial blockage in the catheter 122. Pressure measurements may also be used to determine whether or not the side port 140 has been accessed, as is described below with reference to FIG. 7. The controller 136 may perform a variety of different functions in response to determination that the fluid transfer device 114 is not functioning properly, the catheter 122 is blocked, and/or the side port 140 has been accessed. For example, the controller 136 may actuate an audible alarm 148 that is located within the housing 102 in order to signal that the fluid transfer device 114 is not functioning properly, the catheter 122 is blocked, and/or that the side port 140 has been accessed.

Turning to FIGS. 5 and 6, the exemplary implantable infusion device 100 may be included in an infusion device system 10 that also includes a remote control 200 that is not implanted in the patient. The exemplary remote control 200 includes a housing 202, a touch screen display 204 (or other input device, such as a keypad, with or without a separate display), a battery or other power source 206, a controller 208, such as a microprocessor, microcontroller or other control circuitry, memory 210, and a communication device 212 (including an antenna if necessary). Although the present inventions are not limited to any particular communication device, the exemplary communication device 212 is a telemetry device that transmits an RF signal at a specified frequency. The RF signal may, in some instances, be a carrier signal that carries bit streams. The communication device 212 is configured to send signals to and receive signals from the communication device 132 in the implantable infusion device 100 by way of the antenna 134. Other exemplary communication devices include oscillating magnetic field communication devices, static magnetic field communication devices, optical communication devices, ultrasound communication devices and direct electrical communication devices. In some instances, the remote control may also include an audible alarm 214.

The exemplary remote control 200 may be used to perform a variety of conventional control functions including, but not limited to, turning the infusion device ON or OFF and programming various infusion device parameters. Examples of such parameters include, but are not limited to, the rate of delivery of a given medication, the time at which delivery of a medication is to commence, and the time at which delivery of a medication is to end. Additionally, in at least some implementations, the implantable infusion device 100 will transmit signals to the remote control 200. The signals provide status information about the infusion device 100 that may be stored in memory 210 and/or displayed on the display 204. Examples of such status information include, but are not limited to, the state of charge of the battery 126, the amount of medication remaining in the reservoir 110, the amount of medication that has been delivered during a specified time period, and the presence of a catheter blockage. The signals from the infusion device 100 may also be indicative of sensed physiological parameters in those instances where the infusion device is provided with physiological sensors (not shown).

The exemplary remote control 200 may also be used to initiate a side port monitoring procedure that is performed by the infusion device 100. The side port monitoring procedure allows the clinician to accurately determine whether or not the side port 140 has been accessed by, for example, a hypodermic needle N of a syringe S with a plunger P (FIG. 5).

Referring to FIG. 7, the remote control 200 may be used to send a side port monitoring initiation signal to an infusion device 100 that is implanted within a patient (Step 01). In response to the initiation signal, the infusion device controller 136 will store the pressure currently being sensed by the pressure sensor 144, which is associated with the same passageway 120 as the side port 140, as the baseline pressure (Step 02). The infusion device controller 136 will also use the baseline pressure to calculate one or more threshold pressures against which future pressure measurements will be compared (Step 03) after the monitoring period begins (Step 04). Although infusion devices may be configured to only calculate a high threshold pressure or to only calculate a low threshold pressure, the exemplary infusion device is configured to calculate both high and low threshold pressures.

A high threshold pressure is a pressure that is equal to the baseline pressure plus the magnitude of an expected increase in pressure. The magnitude should be greater than the pressure generated when the fluid transfer device delivers fluid, yet low enough that a clinician can easily generate it by pushing a small volume of fluid (e.g. about 1 ml or less) through a syringe and hypodermic needle and into the side port 140. For example, a pressure increase would typically be at least about 3 psi. A low threshold pressure, on the other hand, is a pressure that is equal to the baseline pressure less the magnitude of the expected decrease in pressure that would result from a clinician withdrawing a small volume of fluid (e.g. about 1 ml or less) from the side port 140 with a syringe and hypodermic needle by pulling on the syringe. Such a pressure decrease would typically be at least about 3 psi. These pressure increases and decreases are outside the range of pressure increases and decreases that could occur during the monitoring period as a result of environmental factors or a catheter blockage, and are within the range of pressure increases and decreases that commonly occur during procedures that involve the side port 140. As such, it may be assumed that pressures which meet or exceed the high and low pressure thresholds are the result of the clinician successfully accessing the side port 140 and infusing or withdrawing fluid.

As opposed to the absolute pressure measurements described above, the high and low threshold pressures may be differential pressures. Here, the baseline pressure is known, but is not calibrated to an absolute pressure in the manner described above. The baseline pressure may instead be set to zero for monitoring purposes. Changes in pressure, and the magnitudes thereof, are monitored from the zero baseline pressure. The high and low threshold pressures are set as a known magnitude of change from the zero baseline pressure, rather than the above-described sum of the absolute baseline pressure and the pressure change.

The side port monitoring period will typically be an amount of time that is sufficient to allow the clinician to transcutaneously insert a hypodermic needle into the side port 140 of an implanted infusion device 100. The monitoring period may, for example, range from about 1 to 5 minutes and may be increased or decreased as desired to suit particular situations.

It should also be noted here that Step 02 and Step 03 will typically be completed within about 1 second after the side port monitoring initiation signal is received by the infusion device 100. As such, Step 04 may, alternatively, occur prior to or simultaneously with Step 02 or prior to or simultaneously with Step 03.

So long as the monitoring period has not expired (Step 05), the infusion device controller 136 will continue to monitor the current pressure sensed by the pressure sensor 144 (Step 06) as the clinician attempts to insert the hypodermic needle into the side port 140. The clinician will either depress or withdraw the syringe plunger when he/she suspects that the hypodermic needle has entered the side port 140. Should the currently monitored pressure increase to a level that is greater than or equal to the high threshold pressure (Step 07), or decrease to a level that is less than or equal to the low threshold pressure (Step 08), the controller 136 will actuate the alarm 148 (Step 09), thereby notifying the clinician that the hypodermic needle has, in fact, been successfully inserted into the side port 140. Alternatively, or in addition, the controller 136 may initiate communication with the remote control 200 that results in actuation of the audible alarm 214 and/or display of a "side port access achieved" message on the display 204. The clinician can then perform the intended diagnostic or therapeutic procedure, e.g. pushing fluid into or drawing fluid from the catheter 122 by way of the side port 140 to check for catheter occlusion, sample cerebrospinal fluid (CSF), inject contrast dye into the patient and/or catheter for use during a fluoroscopic procedure, remove medication from the catheter prior to dye injection, inject additional medication into the target region at the catheter outlet 124 and/or remove pharmaceuticals or other fluids that are causing an allergic or otherwise undesirable biologic reaction. The controller 136 will not, on the other hand, actuate the alarm 148 if the sensed pressure remains between the high and low threshold pressures. The side port monitoring will end after the expiration of the monitoring period (Step 10).

In some implementations, the controller 136 will continue to actuate the alarm 148 so long as the pressure is above the high pressure threshold or below the low pressure threshold. The controller 136 will also de-actuate the alarm 148 when the pressure returns to a level that is between the high and low threshold pressures. If, for example, the clinician stops pushing on the syringe while contrast dye or additional medication is being injected into the patient by way of the side port 140, the alarm 148 will be de-actuated, and will not be re-actuated unless the clinician reinitiates the injection procedure and the needle is in the side port. The alarm 148 will also be de-actuated if the hypodermic needle is inadvertently withdrawn from the side port 140 during an injection or withdrawal procedure. Here, the clinician will have to reinsert the needle into the side port 140, and confirm that the needle has been successfully inserted, in the manner described above.

In the exemplary implementations described above, the functions of monitoring the pressure sensor 144, calculating the threshold pressures, analyzing the sensed pressure, and actuating the alarm 148 are performed by the infusion device controller 136 in combination with instructions that are stored in memory 138. In other implementations, some or all of these functions may be performed by the remote control 200 and, more specifically, by the controller 208 in combination with instructions stored in memory 210. Here, the pressure measurements from the pressure sensor 144 in the infusion device 100 will be transmitted to the remote control 200. For example, and referring to FIGS. 4-6, the clinician may begin the side port monitoring process by pressing a button on the touch screen display 204. The remote control 200 will then instruct the infusion device 100 to begin transmitting signals indicative of the pressure sensed by the sensor 144 to the remote control and to continue transmitting the signals for a defined period, i.e. the monitoring period. The transmission may occur at a frequency of, for example, about once per second. The first pressure signal received by the remote control 200 will be used by the controller 208 to set the baseline pressure and calculate high and low threshold pressures. The controller 208 will also compare subsequently received pressure data to the high and low threshold pressures, and actuate the audible alarm 214 and/or display a "side port access achieved" message on the display 204 if the sensed pressure exceeds the high or low threshold pressures during the monitoring period.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. It is intended that the scope of the present inventions extend to all such modifications and/or additions and that the scope of the present inventions is limited solely by the claims set forth below.

We claim:

1. A method for use with an implanted infusion device and syringe that is not part of the implanted infusion device, the implanted infusion device including an implanted reservoir refill port, an implanted reservoir connected to the implanted reservoir refill port, an implanted pump mechanism connected to the implanted reservoir, an implanted outlet port configured to have a catheter connected thereto, a fluid passage between the implanted pump mechanism and the implanted outlet port that connects the implanted pump mechanism to the implanted outlet port, an implanted side port connected to the fluid passage at a location between the implanted pump mechanism and the implanted outlet port, and a pressure sensor connected to the fluid passage at a location between the implanted pump mechanism and the implanted outlet port, and the syringe including a plunger and a hypodermic needle, the method comprising the steps of:

sensing pressure in the fluid passage between the implanted pump mechanism and the implanted outlet port with the pressure sensor; and determining that the implanted side port has been accessed by the hypodermic needle based on a predetermined change in the pressure in the fluid passage between the implanted pump mechanism and the implanted outlet port sensed by the pressure sensor.

2. A method as claimed in claim 1, further comprising the step of:

providing a visible indication that the side port has been accessed.

3. A method as claimed in claim 1, further comprising the steps of:

sensing a baseline pressure in the fluid passage with the pressure sensor; and monitoring pressure in the fluid passage with the pressure sensor after the baseline pressure measurement has been sensed;

wherein the predetermined change in pressure is a predetermined difference between the baseline pressure and the pressure monitored after the baseline pressure measurement.

4. A method as claimed in claim 3, wherein the predetermined change in pressure comprises a pressure increase from the baseline pressure of a predetermined magnitude.

5. A method as claimed in claim 3, wherein the predetermined change in pressure comprises a pressure decrease from the baseline pressure of a predetermined magnitude.

6. A method as claimed in claim 4, wherein the predetermined change in pressure comprises a pressure increase of at least 3 psi from the baseline pressure.

7. A method for use with an implanted infusion device, a controller, and a syringe that is not part of the implanted infusion device, the implanted infusion device including an implanted reservoir refill port, an implanted reservoir connected to the implanted reservoir refill port, an implanted pump mechanism connected to the implanted reservoir, an implanted outlet port configured to have a catheter connected thereto, a fluid passage between the implanted pump mechanism and the implanted outlet port that connects the implanted pump mechanism to the implanted outlet port, an implanted side port connected to the fluid passage at a location between the implanted pump mechanism and the implanted outlet port, and a pressure sensor connected to the passage at a location between the implanted pump mechanism and the implanted outlet port, the controller being operably connected to the pressure sensor, and the syringe including a plunger and a hypodermic needle, the method comprising the steps of:

sensing a baseline pressure in the fluid passage with the pressure sensor;

continuing to sense pressure with the pressure sensor after the baseline pressure has been sensed;

determining, with the controller, that the hypodermic needle has entered the implanted side port in response to a predetermined decrease in pressure in the fluid passage from the baseline pressure in the fluid passage; and providing an audible and/or visible indication that the side port has been accessed in response to a determination that the hypodermic needle has entered the side port.

8. A method as claimed in claim 7, further comprising the step of:

initiating a side port monitoring period in response to a signal from a remote device;

wherein the predetermined decrease in pressure from a baseline pressure comprises a predetermined decrease in pressure from a baseline pressure that occurs during the side port monitoring period.

9. A method as claimed in claim 7, further comprising the steps of:
   taking a baseline pressure measurement; and
   monitoring pressure after the baseline pressure measurement has been taken.

10. A method as claimed in claim 9, wherein
   monitoring pressure after the baseline pressure measurement has been taken comprises monitoring pressure for at least one minute after the baseline pressure measurement has been taken.

11. A method as claimed in claim 9, further comprising the steps of:
   pulling the syringe plunger while monitoring pressure in the fluid passage after the baseline pressure measurement has been taken.

12. A method as claimed in claim 7, wherein the controller is located within the implanted infusion device.

13. A method as claimed in claim 7, wherein the controller is part of a remote control.

14. A method as claimed in claim 4, further comprising the step of:
   pushing the syringe plunger while monitoring pressure in the fluid passage after the baseline pressure measurement has been taken.

15. A method as claimed in claim 5, further comprising the step of:
   withdrawing the syringe plunger while monitoring pressure in the fluid passage after the baseline pressure measurement has been taken.

16. A method for use with an implanted infusion device, a controller, and a syringe that is not part of the implanted infusion device, the implanted infusion device including an implanted reservoir refill port, an implanted reservoir connected to the implanted reservoir refill port, an implanted pump mechanism connected to the implanted reservoir, an implanted outlet port configured to have a catheter connected thereto, a fluid passage between the implanted pump mechanism and the implanted outlet port that connects the implanted pump mechanism to the implanted outlet port, an implanted catheter access port connected to the fluid passage at a location between the implanted pump mechanism and the implanted outlet port, and a pressure sensor connected to the passage at a location between the implanted pump mechanism and the implanted outlet port, the controller being operably connected to the pressure sensor, and the syringe including a plunger and a hypodermic needle, the method comprising the steps of:
   sensing a baseline pressure in the fluid passage with the pressure sensor;
   continuing to sense pressure with the pressure sensor after the baseline pressure has been sensed;
   determining, with the controller, that the hypodermic needle has entered the implanted catheter access port in response to a predetermined decrease in pressure in the fluid passage from the baseline pressure in the fluid passage; and
   providing an audible and/or visible indication that the catheter access port has been accessed in response to a determination that the hypodermic needle has entered the catheter access port.

17. A method as claimed in claim 16, further comprising the step of:
   initiating a catheter access port monitoring period in response to a signal from a remote device;
   wherein the predetermined decrease in pressure from a baseline pressure comprises a predetermined decrease in pressure from a baseline pressure that occurs during the catheter access port monitoring period.

18. A method as claimed in claim 16, further comprising the steps of:
   taking a baseline pressure measurement; and
   monitoring pressure after the baseline pressure measurement has been taken.

19. A method as claimed in claim 18, wherein
   monitoring pressure after the baseline pressure measurement has been taken comprises monitoring pressure for at least one minute after the baseline pressure measurement has been taken.

20. A method as claimed in claim 18, further comprising the steps of:
   pulling the syringe plunger while monitoring pressure in the fluid passage after the baseline pressure measurement has been taken.

21. A method as claimed in claim 16, wherein the controller is located within the implanted infusion device.

22. A method as claimed in claim 16, wherein the controller is part of a remote control.

* * * * *